(12) United States Patent
Nam et al.

(10) Patent No.: US 10,542,948 B2
(45) Date of Patent: Jan. 28, 2020

(54) MOBILE X-RAY IMAGING APPARATUS

(71) Applicant: Samsung Electronics Co., Ltd., Gyeonggi-do (KR)

(72) Inventors: Jae-won Nam, Yongin-si (KR); Seung-hwan Lee, Yongin-si (KR); Jung-min Kim, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 216 days.

(21) Appl. No.: 15/700,017

(22) Filed: Sep. 8, 2017

(65) Prior Publication Data

US 2018/0110489 A1  Apr. 26, 2018

(30) Foreign Application Priority Data

Oct. 20, 2016 (KR) ........................ 10-2016-0136248
Jan. 20, 2017 (KR) ........................ 10-2017-0009929

(51) Int. Cl.
 *A61B 6/00* (2006.01)
(52) U.S. Cl.
 CPC .............. *A61B 6/4405* (2013.01); *A61B 6/54* (2013.01); *A61B 6/58* (2013.01)
(58) Field of Classification Search
 CPC ........... A61B 6/4405; A61B 6/58; A61B 6/54; A61B 6/586; G01D 5/3473; G01P 3/486
 See application file for complete search history.

(56) References Cited

U.S. PATENT DOCUMENTS

| 4,644,156 | A | 2/1987 | Takahashi et al. |
| 6,670,906 | B1 * | 12/2003 | Roberts ................ G01S 5/0284 342/22 |
| 2007/0139036 | A1 * | 6/2007 | Kondo .................... G01P 3/486 324/179 |
| 2007/0153980 | A1 * | 7/2007 | Butzine ................ A61B 6/4405 378/198 |

(Continued)

FOREIGN PATENT DOCUMENTS

| EP | 2416123 A1 | 2/2012 |
| JP | 2008278935 A | 11/2008 |

OTHER PUBLICATIONS

Communication from a foreign patent office in a counterpart foreign application, European Patent Office, "European Search Report," European Application No. EP 17196263.2, dated Mar. 9, 2018, 7 pages.

*Primary Examiner* — Michael C Bryant

(57) ABSTRACT

A mobile X-ray imaging apparatus includes a main body, a driving wheel provided in a lower portion of the main body and capable of moving the main body, a drive motor configured to drive the driving wheel, a motor encoder configured to detect a rotation speed of the drive motor, a driving wheel rotation state detector configured to detect a rotation state of the driving wheel, the driving wheel rotation state detector comprising a rotation state detection sensor located at the main body, and a bracket coaxially connected to the driving wheel and allowing the rotation state detection sensor to detect an ON/OFF state according to the rotation state of the driving wheel, and a controller configured to control the drive motor based on information detected by the motor encoder and the driving wheel rotation state detector.

18 Claims, 9 Drawing Sheets

(56) References Cited

U.S. PATENT DOCUMENTS

2008/0118036 A1* 5/2008 Jensen ................ A61B 6/4441
378/198
2014/0369477 A1  12/2014 Okuno
2018/0110489 A1* 4/2018 Nam .................... A61B 6/4405

* cited by examiner

MOBILE X-RAY IMAGING APPARATUS

CROSS-REFERENCE TO RELATED APPLICATIONS AND CLAIM OF PRIORITY

This application is related to and claims priority to Korean Patent Application Nos. 10-2016-0136248, filed on Oct. 20, 2016, and 10-2017-0009929, filed on Jan. 20, 2017, in the Korean Intellectual Property Office, the contents of which are incorporated herein by reference.

TECHNICAL FIELD

One or more embodiments relate to a mobile X-ray imaging apparatus having wheels at a lower end thereof and capable of movement.

BACKGROUND

X-rays are electromagnetic waves generally having a wavelength of about 0.01 to 100 angstroms (Å) and properties of penetrating through an object. X-rays have been widely used with medical equipment for imaging the inside of a live body or non-destructive testing equipment used in general industry.

In an X-ray imaging apparatus using an X-ray, X-rays are output by an X-ray source towards an object and an X-ray detector detects a difference in the strength of X-rays transmitted through the object, thereby obtaining an X-ray image of the object. The X-ray image may be used to identify an internal structure of the object and diagnose the object.

In a general X-ray imaging apparatus, since the X-ray source and the X-ray detector are confined to a specific space, a patient needs to visit a test room where the X-ray imaging apparatus is located and position his/her body with respect to the apparatus for X-ray imaging.

However, since patients having difficulty moving are inconvenienced by X-ray imaging using a general X-ray imaging apparatus, mobile X-ray imaging apparatuses capable of obtaining X-ray images regardless of location have been developed.

A mobile X-ray imaging apparatus having a movable main body is disclosed in which an X-ray source mounted on the main body. Using a portable X-ray detector in combination with the X-ray source, the mobile X-ray imaging apparatus may provide X-ray imaging for patients having difficulty moving.

SUMMARY

To address the above-discussed deficiencies, it is a primary object to provide one or more embodiments which include a mobile X-ray imaging apparatus having improved mobility and stability.

Additional aspects will be set forth in part in the description which follows and, in part, will be apparent from the description, or may be learned by practice of the presented embodiments.

According to one or more embodiments, a mobile X-ray imaging apparatus includes a main body, a driving wheel provided in a lower portion of the main body and capable of moving the main body, a drive motor configured to drive the driving wheel, a motor encoder configured to detect a rotation speed of the drive motor, a driving wheel rotation state detector configured to detect a rotation state of the driving wheel, the driving wheel rotation state detector comprising a rotation state detection sensor located at the main body and a bracket coaxially connected to the driving wheel and allowing the rotation state detection sensor to detect an ON/OFF state according to the rotation state of the driving wheel, and a controller configured to control the drive motor based on information detected by the motor encoder and the driving wheel rotation state detector.

The bracket may include a sensor bracket formed along a circumference of the bracket and a plurality of holes formed in the sensor bracket, and the rotation state detection sensor may include first and second sensors arranged adjacent to the sensor bracket.

The first and second sensors may be arranged to satisfy at least three of: a first arrangement state in which the first and second sensors respectively face first and second holes of the plurality of holes at a first position of the bracket, a second arrangement state in which the bracket is rotated by a first angle from the first position to a second position at which the first sensor faces the first hole and the second sensor does not face the second hole, a third arrangement state in which the bracket is rotated by a second angle from the second position to a third position at which the first sensor and the second sensor do not face the first hole and the second hole, respectively, and a fourth arrangement state in which the bracket is rotated by a third angle from the third position to a fourth position at which the first sensor does not face the first hole and the second sensor faces a fourth hole that neighbors the second hole.

The first to third angles may be identical to one another.

The first and second sensors may be light detection sensors.

The controller may determine a rotation direction of the driving wheel based on a detection signal pattern detected by the first and second sensors.

The controller may determine a rotation speed of the driving wheel based on cycles of detection signals detected by the first and second sensors.

The controller may determine an abnormal state of movement of the mobile X-ray imaging apparatus based on information detected by the motor encoder and the driving wheel rotation state detector, and stop driving of the drive motor when an abnormal state is detected.

The mobile X-ray imaging apparatus may further include a control panel having a display displaying an operating state of the mobile X-ray imaging apparatus, in which the controller determines a quasi-abnormal state of movement of the mobile X-ray imaging apparatus based on information detected by the motor encoder and the driving wheel rotation state detector, and displays an attention mark on the display when the quasi-abnormal state is detected.

The mobile X-ray imaging apparatus may further include a warning lamp or a warning sound generator, in which the controller determines a quasi-abnormal state of movement of the mobile X-ray imaging apparatus based on information detected by the motor encoder and the driving wheel rotation state detector, and drives the warning lamp or the warning sound generator when the quasi-abnormal state is detected According to one or more embodiments, a method of operating a mobile X-ray imaging apparatus, the mobile X-ray imaging apparatus including a driving wheel capable of moving a main body and a driving wheel rotation state detector detecting a rotation state of the driving wheel, the method including: measuring a rotation speed of a drive motor by using a motor encoder; and detecting a rotation state of the driving wheel driven by the drive motor, which is performed by the driving wheel rotation state detector, in which the driving wheel rotation state detector includes a rotation state detection sensor located at the main body and a bracket coaxially connected to the driving wheel and allowing the rotation state detection sensor to detect an ON/OFF state according to the rotation state of the driving wheel, and the drive motor is controlled based on information detected by the motor encoder and the driving wheel rotation state detector.

The bracket may include a sensor bracket formed along a circumference of the bracket and a plurality of holes formed in the sensor bracket, and the rotation state detection sensor may include first and second sensors arranged adjacent to the sensor bracket.

The first and second sensors may be arranged to satisfy at least three of: a first arrangement state in which the first and second sensors respectively face first and second holes of the plurality of holes at a first position of the bracket; a second arrangement state in which the bracket is rotated by a first angle from the first position to a second position at which the first sensor faces the first hole and the second sensor does not face the second hole; a third arrangement state in which the bracket is rotated by a second angle from the second position to a third position at which the first sensor and the second sensor do not face the first hole and the second hole, respectively; and a fourth arrangement state in which the bracket is rotated by a third angle from the third position to a fourth position at which the first sensor does not face the first hole and the second sensor faces a fourth hole that neighbors the second hole.

A rotation direction of the driving wheel may be determined based on a detection signal pattern detected by the first and second sensors.

A rotation speed of the driving wheel may be determined based on cycles of detection signals detected by the first and second sensors.

An abnormal state of movement of the mobile X-ray imaging apparatus may be determined based on information detected by the motor encoder and the driving wheel rotation state detector, and when an abnormal state is detected, driving of the drive motor is stopped.

The abnormal state may be a state in which a rotation state of the drive motor exceeds a motor reference value or a rotation state of the driving wheel exceeds a wheel reference value.

A quasi-abnormal state of movement of the mobile X-ray imaging apparatus may be determined based on information detected by the motor encoder and the driving wheel rotation state detector, and when the quasi-abnormal state is detected, an attention mark may be displayed on the display or a warning lamp or a warning sound generator is driven.

The quasi-abnormal state may be a state in which a rotation speed of the drive motor exceeds a first motor reference value, does not exceed a second motor reference value, or a state in which a rotation speed of the driving wheel exceeds a first wheel reference value, and does not exceed a second wheel reference value, and the second motor reference value may be greater than the first motor reference value, and the second wheel reference value may be greater than the first wheel reference value.

When the rotation speed of the drive motor exceeds the second motor reference value or the rotation speed of the driving wheel exceeds the second wheel reference value, driving of the drive motor may be stopped.

In the mobile X-ray imaging apparatus according to an embodiment, movement of the driving wheel is checked by the sensor in addition to the motor encoder when the mobile X-ray imaging apparatus is in motion. Accordingly, double verification of a driving state is performed and thus a dual safety control system may be established.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

FIGS. 1 through 8, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

Terms such as "part" or "portion" stated in the specification may signify a unit to process at least one function or operation and the unit may be embodied by hardware, software, or a combination of hardware and software. In some embodiments, a plurality of parts or portions may be implemented by one unit or element, or a single part or portion may include a plurality of units or elements. The operating principal and embodiments of the present inventive concept are described below with reference to the accompanying drawings.

Also, in the present specification, an "object", which is subject to imaging, may include a human, an animal, or a part of a human or an animal. For example, an object may include a part of a human body such as body organs or a phantom.

Figure 1:
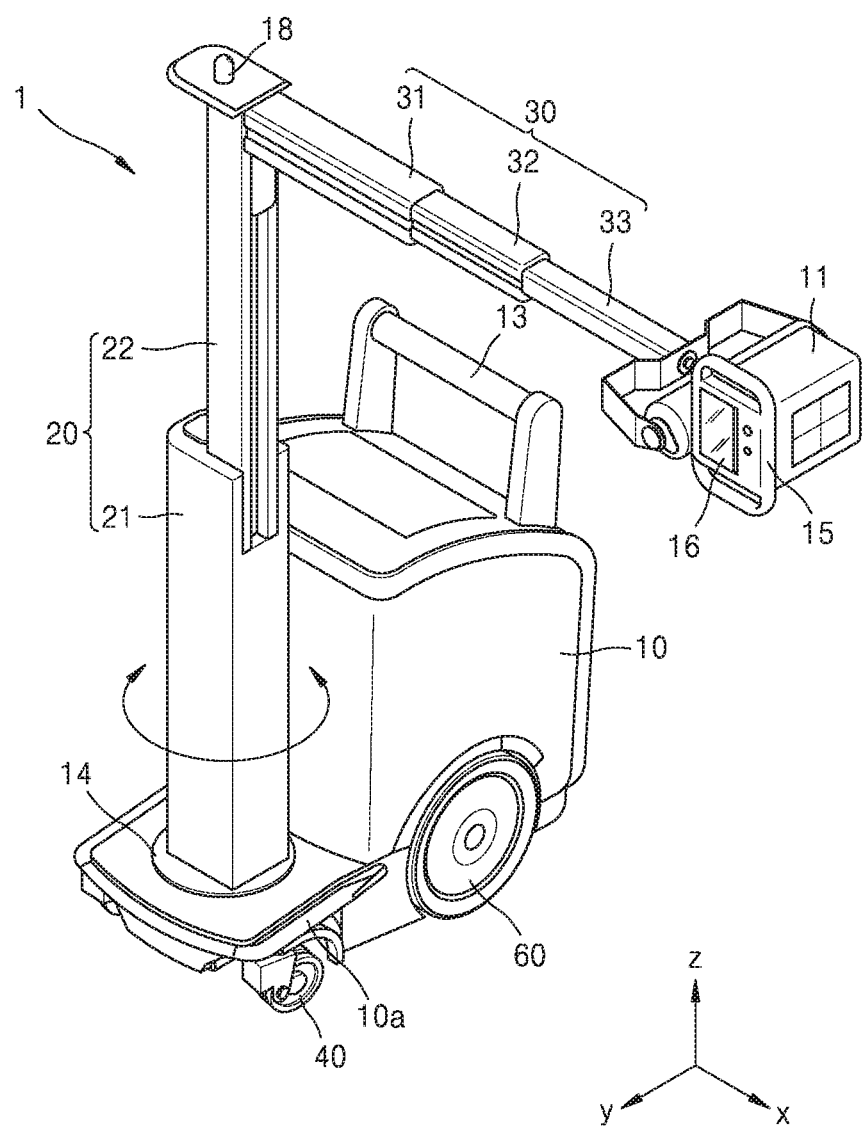
FIG. 1 illustrates a perspective view of a mobile X-ray imaging apparatus according to an embodiment.

FIG. 1 illustrates a perspective view of a mobile X-ray imaging apparatus 1 according to an embodiment.

Referring to FIG. 1, the mobile X-ray imaging apparatus 1 according to the present embodiment may include a main body 10 and an X-ray source 11 mounted on the main body 10.

A movable wheel 40 and a driving wheel 60 may be provided in a lower portion of the main body 10. The main body 10 may include a handle 13, and a user may move the main body 10 by holding and pushing or pulling the handle 13. In FIG. 1, a direction in which the user pushes the handle 13 to move the mobile X-ray imaging apparatus 1 forward is a y direction, and a direction in which the user pulls the handle 13 to move the mobile X-ray imaging apparatus 1 back is a −y direction. The movable wheel 40 may be located in a direction in which the main body 10 moves forward, that is, at a front side, and the driving wheel 60 may be located to the rear of the movable wheel 40. The driving wheel 60 may receive a driving force from a drive motor 95 of FIG. 6. Although FIG. 1 illustrates two movable wheels as the movable wheel 40, the present disclosure is not limited thereto. For example, only one movable wheel may be provided as the movable wheel 40.

The main body 10 may include a control panel 15. The user may control the operation of the mobile X-ray imaging apparatus 1 via the control panel 15. The control panel 15 may be provided with a display 16 to display an operating state of the mobile X-ray imaging apparatus 1. The display 16 may display an inspection notification or draw user's attention through an indication lamp by displaying a message such as "Service check required", as described below, when a quasi-abnormal state is detected during movement of the mobile X-ray imaging apparatus 1.

Although FIG. 1 illustrates a configuration in which the control panel 15 is arranged adjacent to the X-ray source 11, the present disclosure is not limited thereto. For example, the control panel 15 may be provided on the main body 10 or may be supported by a control panel support member extending from the main body 10.

The main body 10 may be provided with a column 20 having a pillar shape. The column 20 may include an arm 30 extending in a direction away from the column 20, and the X-ray source 11 may be mounted on the arm 30.

A rotatable panel 14 may be rotatably provided on the main body 10. The column 20 may be mounted on the rotatable panel 14. A front lower end 10a of the main body 10 may protrude from the main body 10 and support the rotatable panel 14. The column 20 may rotate with the rotatable panel 14. As the column 20 rotates, the X-ray source 11 connected to the column 20 may rotate and thus a position of the X-ray source 11 may vary. As such, as the X-ray source 11 is provided to have a variable position, X-ray imaging may be performed at various angles.

The column 20 may be capable of vertically extending or retracting. As the column 20 extends or retracts, the position of the X-ray source 11 connected to the column 20 may vertically vary. As such, as the X-ray source 11 is provided such that the position of the X-ray source 11 may vertically vary, X-ray imaging may be performed at various heights.

In an example, the column 20 may include a first column 21 and a second column 22 that is extendable from the first column 21. The second column 22 may be capable of sliding along the first column 21. As the second column 22 slides upward along the first column 21, the length of the column 20 may increase. As the second column 22 slides down along the first column 21, the length of the column 20 may decrease.

The arm 30 may be mounted on the second column 22. The arm 30 may slidably extend from the second column 22. As the arm 30 slides along the second column 22, the vertical position of the X-ray source 11 may vary.

The arm 30 may be extendable, and the X-ray source 11 may be mounted on an end of the arm 30. As the arm 30 extends or retracts, the X-ray source 11 may move sideways and thus the position of the X-ray source 11 may vary in a horizontal direction.

In an example, the arm 30 may further include a first arm 31 capable of slidably extending from the second column 22 and a second arm 32 capable of extending from the first arm 31. Furthermore, the arm 30 may further include a third arm 33 capable of extending from the second arm 32. The X-ray source 11 may be mounted on an end portion of the third arm 33. As the second arm 32 and/or the third arm 33 slides from the first arm 31 in one direction or in the opposite direction, the length of the arm 30 may increase or decrease. The configuration of the arm 30 is not limited to the above description.

The column 20 and/or the arm 30 may include a separate drive source for extending or retracting the column 20 and/or the arm 30, or may be manually extended or retracted without a separate drive source.

A warning lamp 18 may be additionally mounted on an upper end of the column 20, that is, on an upper end of the second column 22. The warning lamp 18 may emit light a light of a specific color, for example, red light, when a driving state of the mobile X-ray imaging apparatus 1 is determined to be in an abnormal state, as described below. The warning lamp 18 may designed to emit a plurality of color lights and thus the warning lamp 18 may emit one color light, for example, green light, when the mobile X-ray imaging apparatus 1 is in a driving state, and/or emit another color light, for example, orange light, when the mobile X-ray imaging apparatus 1 performs X-ray imaging. The warning lamp 18 is only an example, and a warning sound generator (not shown) may be provided with the warning lamp 18 or instead of the warning lamp 18. Accordingly, the warning sound generator may generate a warning sound when the mobile X-ray imaging apparatus 1 is determined to be in an abnormal driving state.

To power movement of the mobile X-ray imaging apparatus 1 according to the present embodiment, the main body 10 may have a power source or may be connected to an external power cable to receive power.

Figure 2:
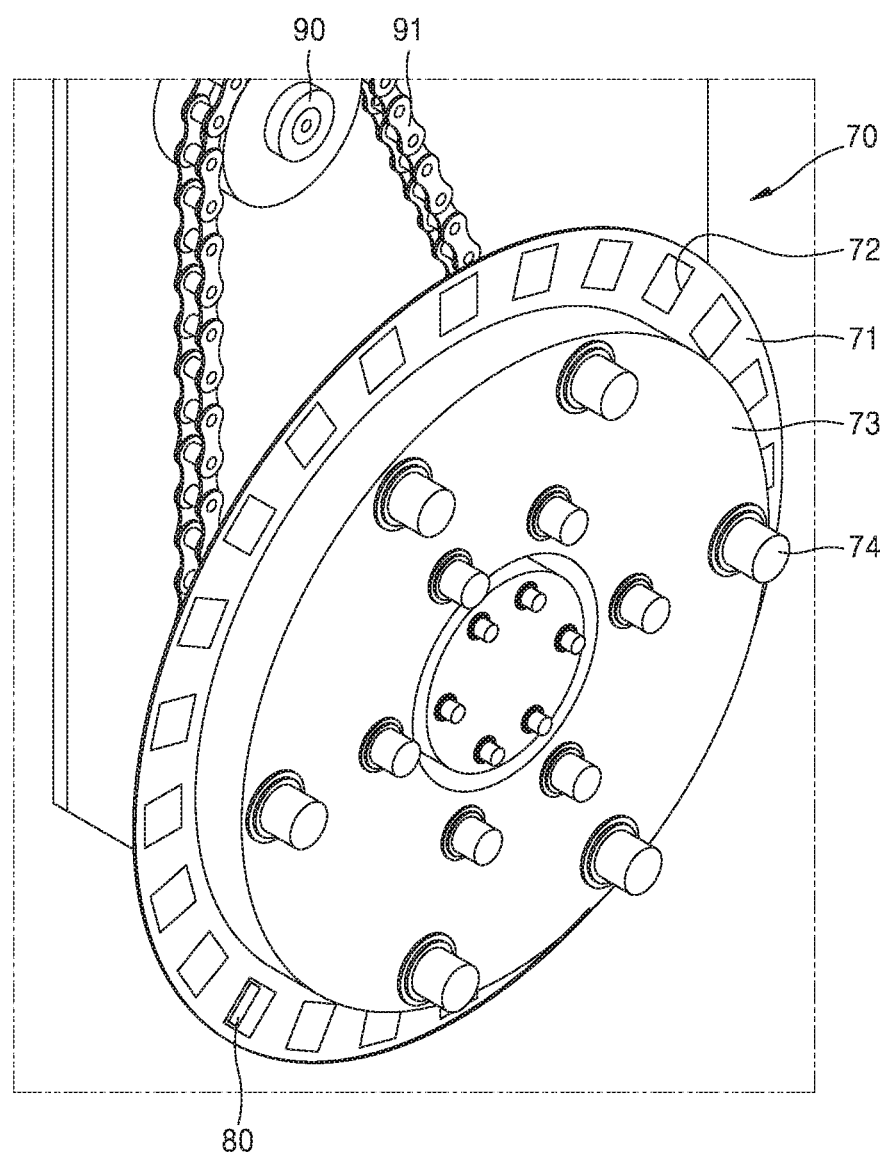
FIG. 2 illustrates an enlarged perspective view of a portion exposed by removing the driving wheel of the mobile X-ray imaging apparatus of FIG. 1.
Figure 3A:
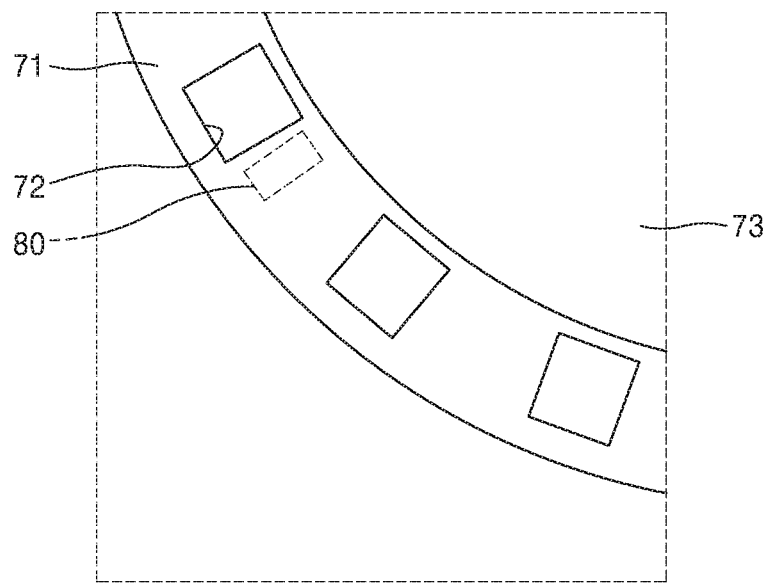
FIGS. 3A and 3B illustrate the positions of a sensor according to a rotation position of the driving wheel.
Figure 3B:
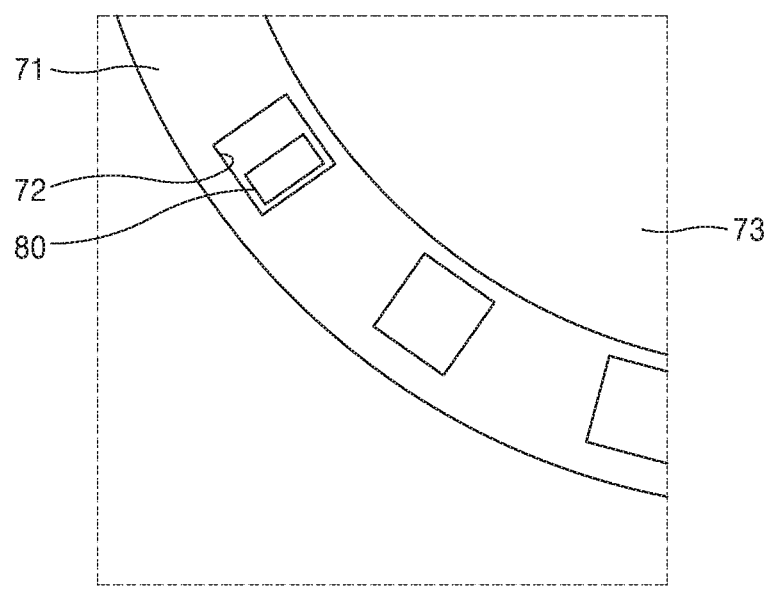

FIG. 2 illustrates an enlarged perspective view of a portion exposed by removing the driving wheel 60 of the mobile X-ray imaging apparatus 1 of FIG. 1. FIGS. 3A and 3B illustrate the positions of a sensor according to a rotation position of the driving wheel.

Figure 6:
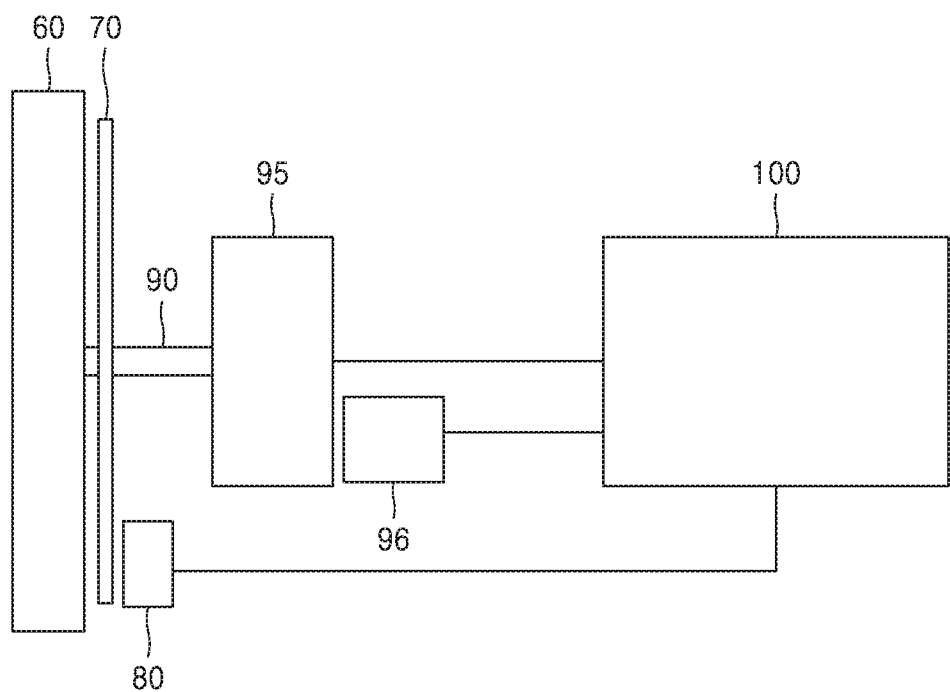
FIG. 6 illustrates a block diagram of a mobile X-ray imaging apparatus according to an embodiment.

Referring to FIG. 2, a bracket 70 connecting a drive shaft 90 of FIG. 6 and the driving wheel 60 is located inside the driving wheel 60. The bracket 70 may include a wheel fixing plate 73 fixing a position of the driving wheel 60. The wheel fixing plate 73 may have, for example, a disc shape, and a center portion of the wheel fixing plate 73 may be coupled to the drive shaft 90. A coupling member 74 is provided on the wheel fixing plate 73 and coupled to the driving wheel 60. A sensor bracket 71 is provided on an outer circumference of the wheel fixing plate 73. The sensor bracket 71 may be formed of a material having reflectivity such as metal, or at least an inner side surface of the sensor bracket 71 facing a hole sensing sensor 80 may be coated with a material having reflectivity. The sensor bracket 71 may be integrally formed with the wheel fixing plate 73. In some example embodiments, the sensor bracket 71 may be separately provided coaxially with the wheel fixing plate 73. A plurality of holes 72 are provided at regular intervals along the edge of the sensor bracket 71. The holes 72 may have the same shape, for example, a square shape as illustrated in FIG. 2.

The hole sensing sensor 80 for sensing the holes 72 may be provided at one side of the sensor bracket 71. The hole sensing sensor 80 may be a light detection sensor such as a photo sensor detector (PSD). The combination of the sensor bracket 71, the holes 72, and the hole sensing sensor 80 may be an example of a driving wheel rotation state detector for detecting ON/OFF states according to a rotation state of the driving wheel 60. The hole sensing sensor 80 may include first and second sensors 81 and 82 (see FIGS. 4A to 4D) arranged adjacent to the inner side surface of the sensor bracket 71. In the present embodiment, although the hole sensing sensor 80 including two sensors 81 and 82 is described, the hole sensing sensor 80 may include one sense or three or more sensors.

The wheel fixing plate 73 is rotated by receiving the driving force from the drive motor 95 of FIG. 6 via the drive shaft 90 and a drive chain 91. The drive chain 91 may be omitted, and the wheel fixing plate 73 may be directly connected to the drive shaft 90. The drive motor 95 may further include a motor encoder 96 (see FIG. 6) and a break (not shown). Furthermore, the drive motor 95 may be further provided with a gearbox (not shown).

FIG. 3A illustrates that the hole sensing sensor 80 is located at a position of the sensor bracket 71 that does not match any of the holes 72. FIG. 3B illustrates that the hole sensing sensor 80 is located at a position of the sensor bracket 71 that matches one of the holes 72. In the present embodiment, no separate light-emitting device may be arranged, and thus the hole sensing sensor 80 may detect ambient light. When the hole sensing sensor 80 directly faces the inner side surface of the sensor bracket 71 as shown in FIG. 3A, the hole sensing sensor 80 may detect the light reflected from the inner side surface of the sensor bracket 71. Also, when the hole sensing sensor 80 faces the holes 72 of the sensor bracket 71 as shown in FIG. 3B, the hole sensing sensor 80 may be unable to detect the light reflected from the inner side surface of the sensor bracket 71. Accordingly, as the amount of light detected by the hole sensing sensor 80 at the position of FIG. 3A is relatively greater than the amount of light detected by the hole sensing sensor 80 at the position of FIG. 3B, the hole sensing sensor 80 at the position of FIG. 3A is ON, and the hole sensing sensor 80 at the position of FIG. 3B is OFF.

When the ambient light is very weak, a light-emitting device (not shown) may be arranged adjacent to the hole sensing sensor 80. The light-emitting device and the hole sensing sensor 80 may be located on the same surface of the sensor bracket 71. In this example, when the light reflected from the light-emitting device is detected by the hole sensing sensor 80, the hole sensing sensor 80 is ON. When the light reflected from the light-emitting device is not detected by the hole sensing sensor 80, the hole sensing sensor 80 is OFF. The light-emitting device and the hole sensing sensor 80 may be located at the opposite surfaces of the sensor bracket 71. In this example, the ON/OFF states may be reversed.

FIGS. 4A to 4D illustrate an exemplary configuration that the first and second sensors 81 and 82 are arranged at the sensor bracket 71.

Figure 4A:
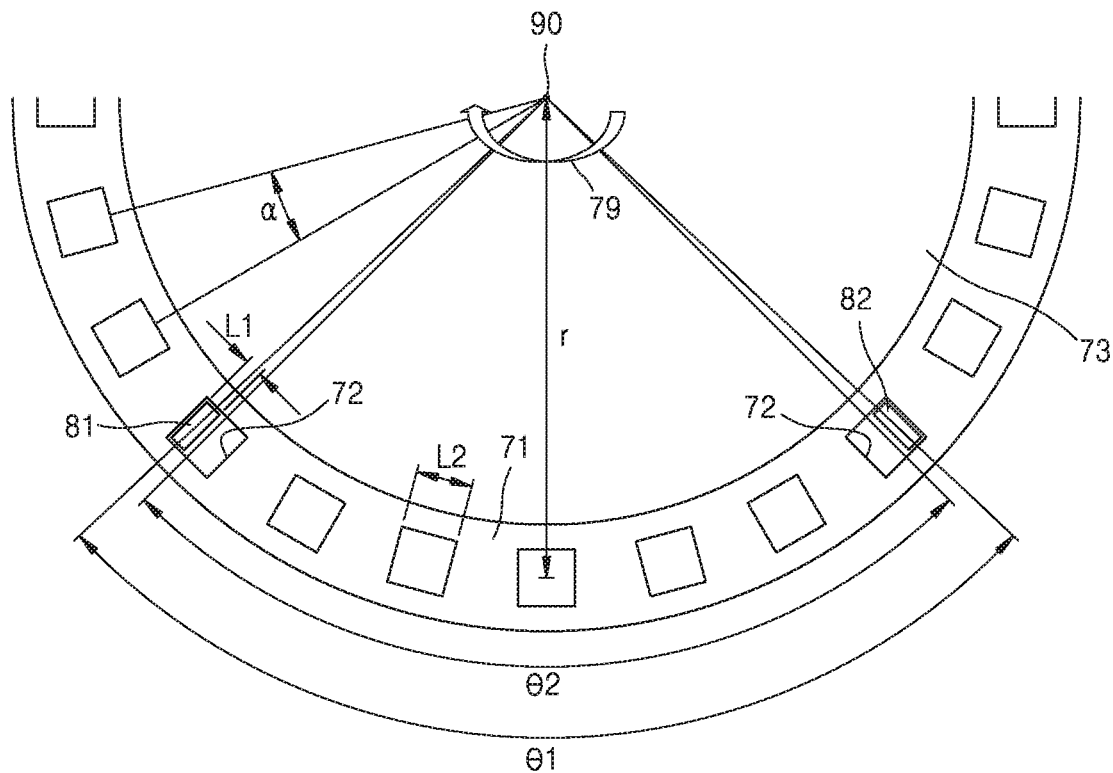
FIGS. 4A to 4D illustrate an example of an operation of the sensor according to the rotation position of the driving wheel.

A sensor surface for detecting light of each of the first and second sensors 81 and 82 may have a length L1 in a circumferential direction, as illustrated in FIG. 4A. Each of the holes 72 may have a length L2 in the circumferential direction. The lengths L1 and L2 may satisfy Mathematical Expression 1 below.

$$0 < L1 < \frac{L2}{2} \qquad \text{<Mathematical Expression 1>}$$

The holes 72 are spaced apart by the size of the holes 72 from one another in the circumferential direction. In other words, an angle α between the centers of the holes 72 that neighbor each other with respect to the drive shaft 90 may be given as follows.

$$\alpha = 2 \times \frac{L2}{r} \qquad \text{<Mathematical Expression 2>}$$

In Mathematical Expression 2, "r" denotes a distance between each of the holes 72 and the drive shaft 90.

The first and second sensors 81 and 82 are arranged such that an angle between the centers of the sensor surfaces has an angle θ1 with respect to the drive shaft 90. An interval between the centers of the holes 72 corresponding to the first and second sensors 81 and 82 has an angle θ2 with respect to the drive shaft 90. The angle θ2 is an integer multiple of the angle α between the neighboring holes 72. FIG. 4A illustrates an example embodiment when the angle θ2 is 6α.

The angles θ1 and θ2 may satisfy Mathematical Expression 3 below.

$$\theta1 = \theta2 - \frac{\alpha}{4} \qquad \text{<Mathematical Expression 3>}$$

Next, in the exemplarily illustrated arrangements of FIGS. 4A to 4D, the detection signals of the first and second sensors 81 and 82 are described.

Figure 4B:
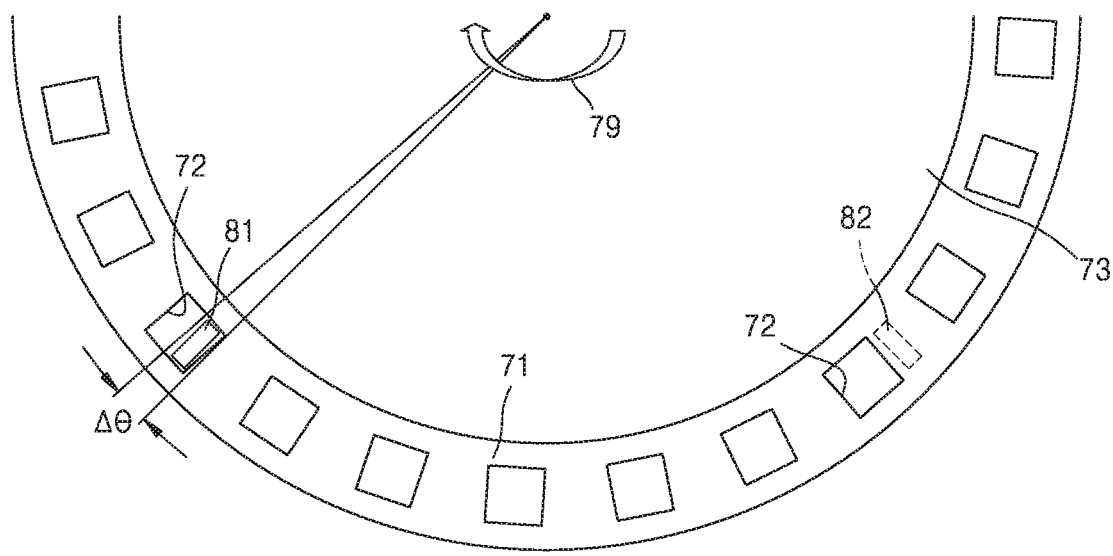

As illustrated in FIG. 4A, at a time point, the first and second sensors 81 and 82 may be simultaneously located at the positions of the holes 72 (first arrangement state). In this example, both the first and second sensors 81 and 82 detect OFF signals. Next, as illustrated in FIG. 4B, when the sensor bracket 71 rotates by an angle Δθ in a clockwise direction 79, the first sensor 81 still remains at the position of the holes 72, but the second sensor 82 is hidden by the sensor bracket 71 (second arrangement state). The first sensor 81 detects an OFF signal, whereas the second sensor 82 detects an ON signal. The angle Δθ is an angle corresponding to the rotation of the sensor bracket 71 while the ON/OFF state of any one of the first and second sensors 81 and 82 is changed. In the present embodiment, the angle Δθ may be given as shown in Mathematical Expression 4 below.

$$\Delta\theta = \theta2 - \theta1 = \frac{\alpha}{4}$$ <Mathematical Expression 4>

The angle Δθ may vary according to the number, position, and size of each of the first and second sensors 81 and 82, the shape, number, and size of each of the holes 72, and the diameter of the sensor bracket 71.

Figure 4C:
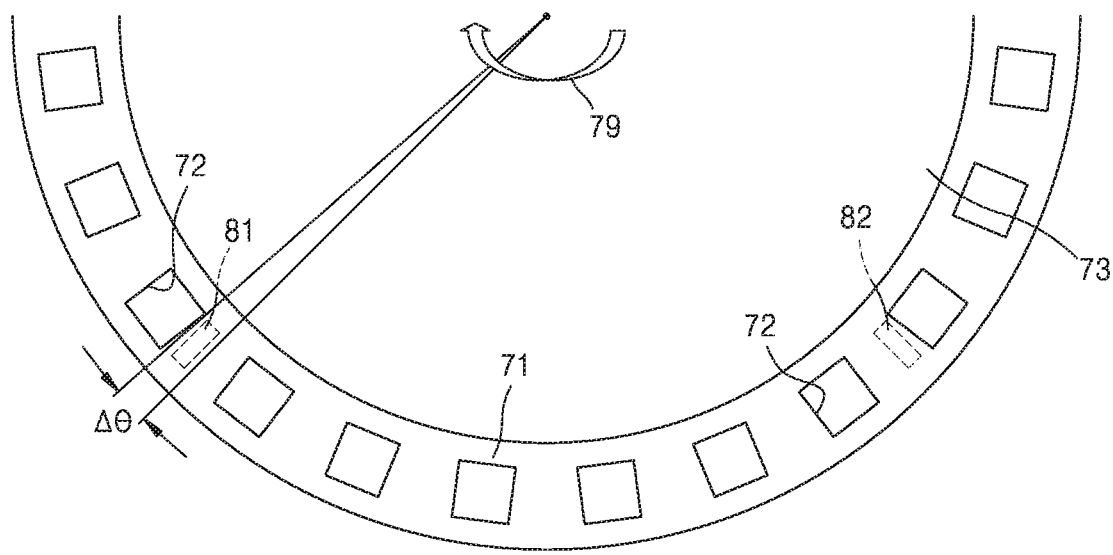
Figure 4D:
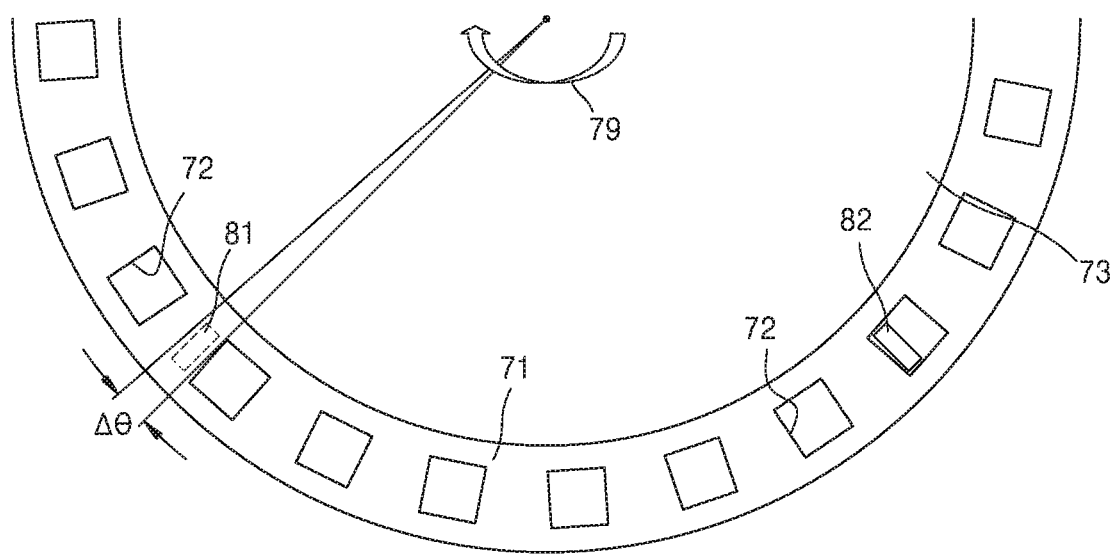
Figure 5A:
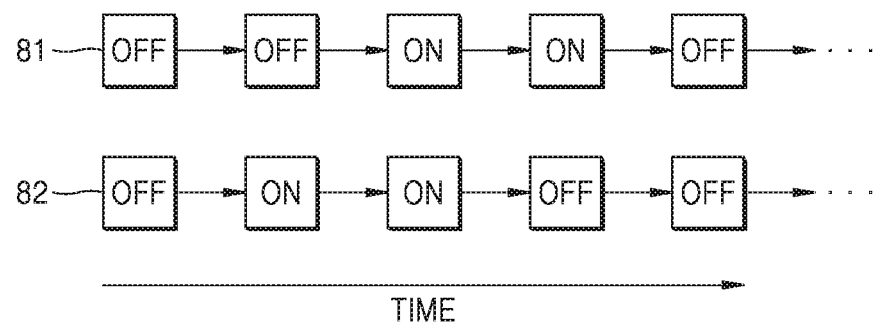
FIGS. 5A and 5B illustrate detection signals of first and second sensors according to rotation of a bracket.

As illustrated in FIG. 4C, when the sensor bracket 71 further rotates in the clockwise direction 79 by the angle Δθ, both the first and second sensors 81 and 82 are hidden by the sensor bracket 71 (third arrangement state) and may detect ON signals. When the sensor bracket 71 further rotates in the clockwise direction 79 by the angle Δθ as illustrated in FIG. 4D, the first sensor 81 is still hidden by the sensor bracket 71 and the second sensor 82 is located at the position of the holes 72 (fourth arrangement state), in which the first sensor 81 may detect an ON signal and the second sensor 82 may detect an OFF signal. When the sensor bracket 71 further rotates in the clockwise direction 79 by the angle Δθ, the first and second sensors 81 and 82 are in the first arrangement state of FIG. 4A. In other words, as the sensor bracket 71 rotates in the clockwise direction 79, the first and second sensors 81 and 82 may detect signals in an order of (OFF, OFF), (OFF, ON), (ON, ON), (ON, OFF), (OFF, OFF), . . . , as illustrated in FIG. 5A.

Figure 5B:
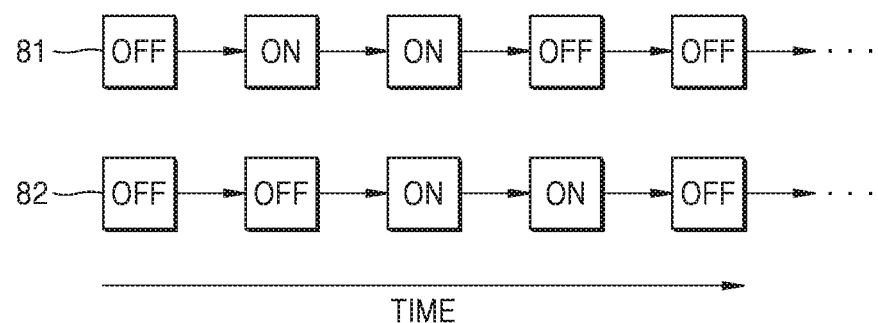

When the rotation direction of the sensor bracket 71 is reversed, the order of the ON/OFF state combination of the first and second sensors 81 and 82 described in FIGS. 4A to 4D may be reversed as well. In other words, as the sensor bracket 71 rotates in the reverse clockwise direction, the first and second sensors 81 and 82 may sequentially detect signals in an order of (OFF, OFF), (ON, OFF), (ON, ON), (OFF, ON), (OFF, OFF), . . . , as illustrated in FIG. 5B.

Accordingly, the rotation direction of the sensor bracket 71 may be detected from a pattern of the signals detected by the first and second sensors 81 and 82.

Furthermore, since the time interval of ON/OFF signals detected by the first and second sensors 81 and 82 may be determined by the rotation speed of the rotation speed of the sensor bracket 71 and the diameter of the sensor bracket 71, the speed of the sensor bracket 71 may be detected from the time interval of the ON/OFF signals detected by the first and second sensors 81 and 82.

The shape or arrangement of the driving wheel rotation state detector illustrated in FIGS. 4A to 4D, that is, the combination of the sensor bracket 71, the holes 72 and the hole sensing sensor 80, is exemplary, and the present disclosure is not limited thereto. For example, the holes 72 may have a rectangular, circular, or oval shape.

Furthermore, by varying the arrangement of the first and second sensors 81 and 82, any one of the first to fourth arrangement states illustrated in FIGS. 4A to 4D may not be satisfied. In other words, the first and second sensors 81 and 82 may be arranged to satisfy at least three arrangement states of the first to fourth arrangement states illustrated in FIGS. 4A to 4D. In this example, since the pattern of the ON/OFF signals varies according to the rotation direction, the rotation direction may be detected.

Furthermore, although in the present embodiment the rotation angles of the sensor bracket 71 when changed to the first to fourth arrangement states are all the same as Δθ, the present disclosure is not limited thereto. According to the size of the sensor surfaces of the first and second sensors 81 and 82 or the sizes of the holes 72, at least some of the rotation angles of the sensor bracket 71 when changed to the first to fourth arrangement states may be different from other rotation angles.

Furthermore, the hole sensing sensor 80 may include three or more sensors and thus the ON/OFF states may be combined in more various ways.

Next, the operation of the mobile X-ray imaging apparatus 1 of the present embodiment is described with reference to FIG. 6.

FIG. 6 illustrates a block diagram of the mobile X-ray imaging apparatus 1 according to an embodiment.

Referring to FIG. 6, the mobile X-ray imaging apparatus 1 may include the driving wheel 60, the drive shaft 90 for transferring a driving force to the driving wheel 60, the drive motor 95 for supplying the driving force, and a motor encoder 96 for detecting the rotation speed of the drive motor 95. A controller 100 may control the driving of the drive motor 95. Furthermore, the controller 100 may detect an emergency situation through the rotation speed of the drive motor 95 detected by the motor encoder 96, and may stop the driving of the drive motor 95. For example, when the rotation speed of the drive motor 95 detected by the motor encoder 96 suddenly increases too fast or suddenly stops, such a state may be considered as a mechanical malfunction or glitch and thus the driving of the drive motor 95 may be stopped for safety.

Furthermore, in the mobile X-ray imaging apparatus 1 of the present embodiment, the driving wheel rotation state detector is arranged at the side of the bracket 70 for fixing the driving wheel 60 and thus the driving speed and the driving direction are separately detected at the side of the driving wheel 60. The configuration of the driving wheel rotation state detector such as the sensor bracket 71/the holes 72 and the hole sensing sensor 80 suggested in the present embodiment is very stable even though accuracy in the driving speed is slightly low. Compared to the rotation speed of the drive motor 95 detected by the motor encoder 96, an abnormal driving of the drive motor 95 may be detected more stably.

When the state of a drive motor is detected with a motor encoder only in a mobile X-ray imaging apparatus according to the related art, determination error in the motor encoder may cause a problem in the control of the mobile X-ray imaging apparatus, and thus a safety accident may directly occur. For example, while the drive motor 95 is currently driven at an abnormal speed, the motor encoder fails to recognize the abnormal state, or separately from the drive motor 95 the driving wheel 60 may move at an abnormal speed.

In the present embodiment, as the very stable driving wheel rotation state detector is arranged at the side of the driving wheel, not a single control of the motor encoder, but a parallel control of an additional separate physical checking apparatus may constitute a dual safety control system and thus more stable use environment may be provided to users.

Figure 7:
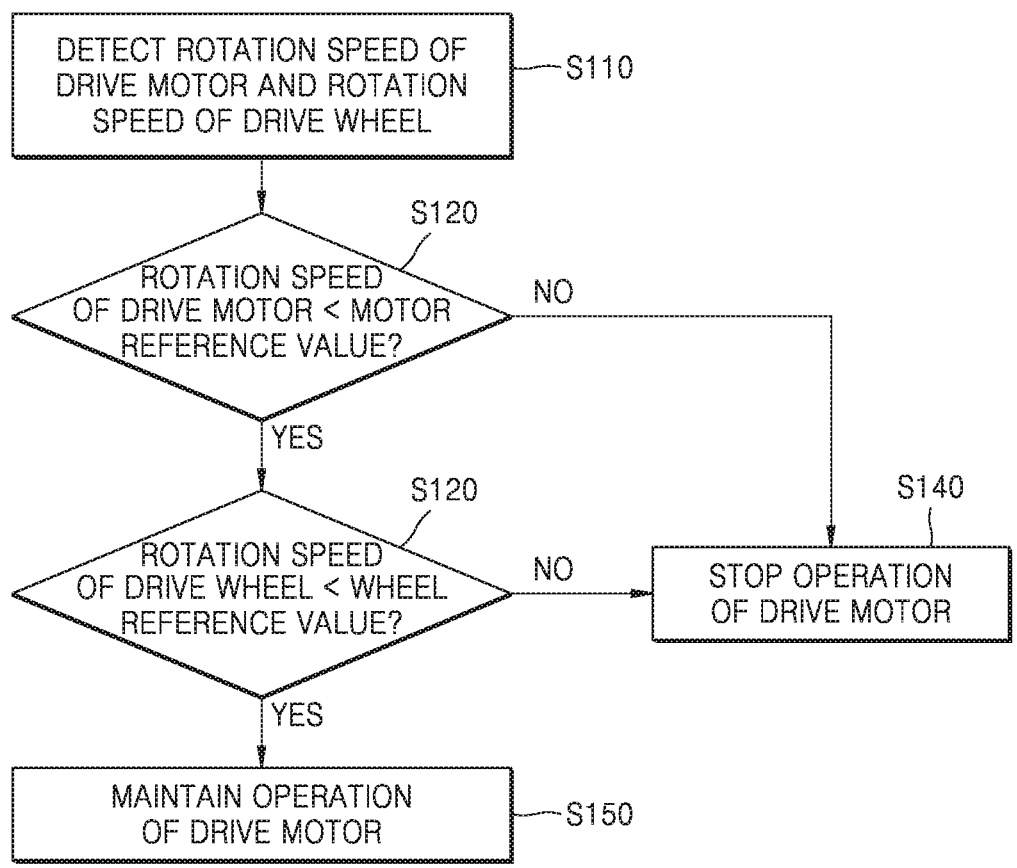
FIG. 7 illustrates a method of operating a mobile X-ray imaging apparatus, according to an embodiment.

FIG. 7 illustrates a method of operating the mobile X-ray imaging apparatus 1, according to an embodiment.

Referring to FIG. 7, when the drive motor 95 of the mobile X-ray imaging apparatus 1 is operated, the rotation speed of the drive motor 95 is continuously or discontinuously detected by the motor encoder 96 (S110). Furthermore, the rotation state of the driving wheel 60 is detected by driving wheel rotation state detector simultaneously with the detection of the rotation speed of the drive motor 95 or at a preset cycle (S120). The rotation state of the driving wheel 60 may include the rotation direction and the rotation speed of the driving wheel 60.

As such, the controller 100 may determine whether the driving state of the mobile X-ray imaging apparatus 1 is abnormal or not, based on information of the detected rotation speed of the drive motor 95 and the detected rotation state of the driving wheel 60. For example, when the rotation speed of the drive motor 95 detected by the motor encoder 96 exceeds a motor reference value (S120), it may be determined that the drive motor 95 is driven in an abnormal state. Furthermore, when the rotation speed of the driving wheel 60 exceeds a wheel reference value (S130), it may be determined that the mobile X-ray imaging apparatus 1 is driven in an abnormal state. Also, when the mobile X-ray imaging apparatus 1 moves forward, but the rotation direction of the driving wheel 60 is in the opposite direction, it may be determined that the mobile X-ray imaging apparatus 1 is driven in an abnormal state. Accordingly, when at least one of the rotation speed of the drive motor 95 detected by the motor encoder 96 and the rotation speed detected by the driving wheel 60 exceeds a certain reference value, the controller 100 may instantly stop the driving of the drive motor 95 and/or generate a warning sound or turn on a warning lamp (S140), by which an accident may be prevented. When the motor encoder 96 abnormally operates, the rotation speed of the drive motor 95 is not correctly detected and thus an abnormal driving of the drive motor 95 may be caused or the abnormal driving of the drive motor 95 may not be detected. When each of the rotation speed of the drive motor 95 detected by the motor encoder 96 and the rotation speed detected by the driving wheel 60 satisfies the reference value, the driving of the drive motor 95 is maintained (S150).

Figure 8:
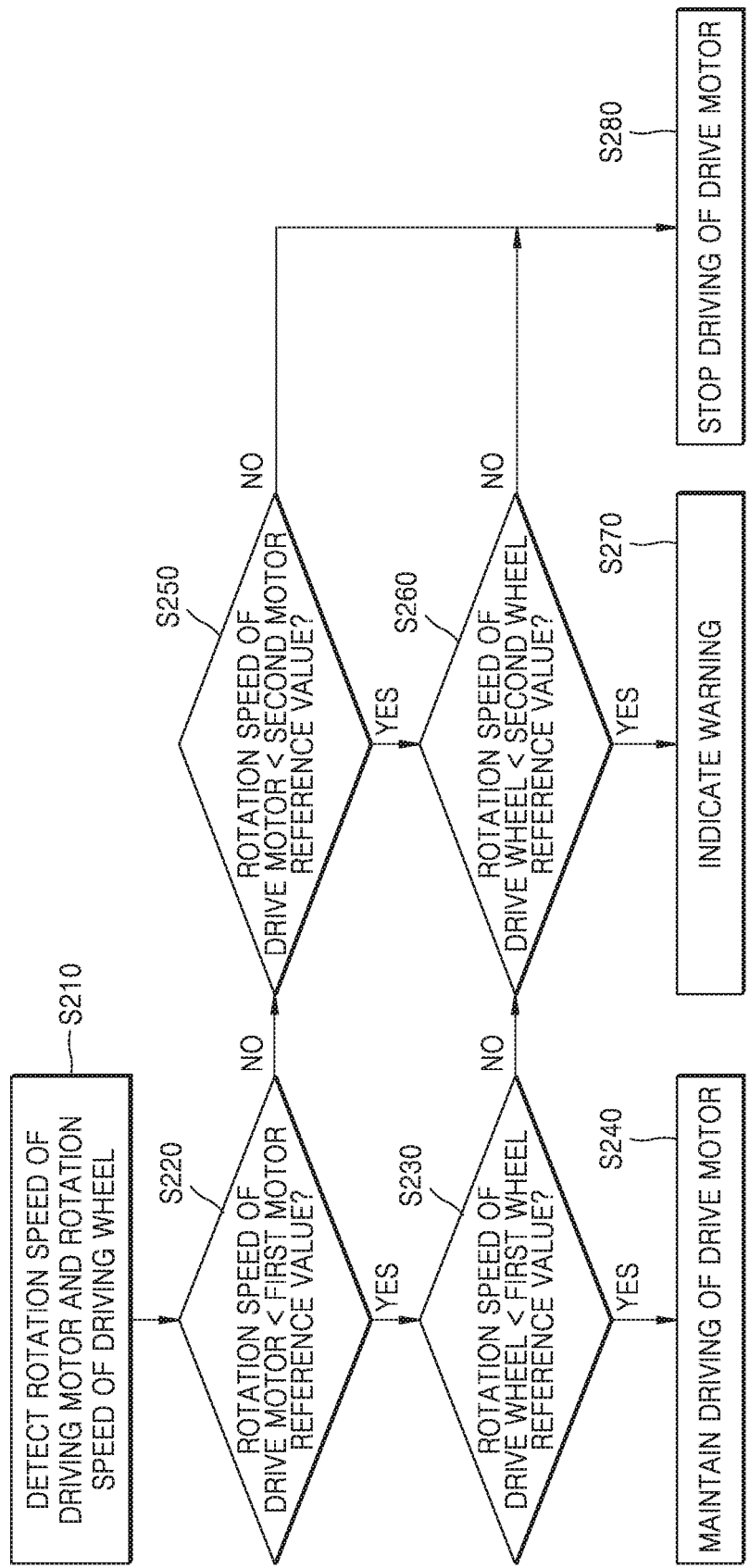
FIG. 8 illustrates a method of operating a mobile X-ray imaging apparatus, according to another embodiment.

FIG. 8 illustrates a method of operating the mobile X-ray imaging apparatus 1, according to another embodiment. As described above, the mobile X-ray imaging apparatus 1 of the present embodiment may detect the rotation speed of the drive motor 95 by means of the motor encoder 96, and detect the rotation state of the driving wheel 60 by means of the driving wheel rotation state detector (S210). The rotation state of the driving wheel 60 may include the rotation direction and the rotation speed of the driving wheel 60.

The controller 100 may set the multiple reference values. For example, a motor reference value may include a first motor reference value and a second motor reference value of a low level, and a wheel reference value may include a first wheel reference value and a second wheel reference value of a low level. When the rotation speed of the drive motor 95 detected by the motor encoder 96 is less than or equal to the first motor reference value (S220) and the rotation speed detected by the driving wheel 60 is less than or equal to the first wheel reference value (S230), the movement of the mobile X-ray imaging apparatus 1 is determined to be a normal state and thus the driving of the drive motor 95 is maintained (S240). When the rotation speed of the drive motor 95 detected by the motor encoder 96 exceeds the first motor reference value (S220), and the rotation speed of the drive motor 95 does not exceed the second motor reference value (S250), the driving of the drive motor 95 may be determined to be a quasi-abnormal state. Furthermore, when the rotation speed detected by the driving wheel 60 exceeds the first wheel reference value, and the rotation speed of the driving wheel 60 does not exceed the second wheel reference value (S260), the rotation of the driving wheel 60 may be determined to be in a quasi-abnormal state. As such, when the driving of the drive motor 95 or the rotation of the driving wheel 60 are in a quasi-abnormal state, inspection notification may be displayed or user's attention is drawn through a warning sound or an indication lamp indicating a message such as "Service check required" (S270). Furthermore, when the rotation speed of the drive motor 95 detected by the motor encoder 96 exceeds the second motor reference value (S250) or the rotation speed of the driving wheel 60 exceeds the second wheel reference value (S260), the driving of the drive motor 95 may be instantly stopped and/or the warning sound may be generated or the warning lamp may be operated (S280).

It should be understood that embodiments described herein should be considered in a descriptive sense only and not for purposes of limitation. Descriptions of features or aspects within each embodiment should typically be considered as available for other similar features or aspects in other embodiments.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A mobile X-ray imaging apparatus comprising:
   a main body;
   a driving wheel provided in a lower portion of the main body and capable of moving the main body;
   a drive motor configured to drive the driving wheel;
   a motor encoder configured to detect a rotation speed of the drive motor;
   a driving wheel rotation state detector configured to detect a rotation state of the driving wheel, the driving wheel rotation state detector comprising:
   a rotation state detection sensor located at the main body, and
   a bracket coaxially connected to the driving wheel and allowing the rotation state detection sensor to detect an ON/OFF state according to the rotation state of the driving wheel; and
   a controller configured to control the drive motor based on information detected by the motor encoder and the driving wheel rotation state detector,
   wherein the controller is further configured to determine an abnormal state of movement of the mobile X-ray imaging apparatus based on information detected by the motor encoder and the driving wheel rotation state detector, and stop driving of the drive motor when an abnormal state is detected.

2. The mobile X-ray imaging apparatus of claim 1, wherein the bracket comprises a sensor bracket formed along a circumference of the bracket and a plurality of holes formed in the sensor bracket, and wherein the rotation state detection sensor comprises first and second sensors arranged adjacent to the sensor bracket.

3. The mobile X-ray imaging apparatus of claim 2, wherein the first and second sensors are arranged to satisfy three or more of:
  a first arrangement state in which the first and second sensors respectively face first and second holes of the plurality of holes at a first position of the bracket;
  a second arrangement state in which the bracket is rotated by a first angle from the first position to a second position at which the first sensor faces the first hole and the second sensor does not face the second hole;
  a third arrangement state in which the bracket is rotated by a second angle from the second position to a third position at which the first sensor and the second sensor do not face the first hole and the second hole, respectively; or
  a fourth arrangement state in which the bracket is rotated by a third angle from the third position to a fourth position at which the first sensor does not face the first hole and the second sensor faces a fourth hole that neighbors the second hole.

4. The mobile X-ray imaging apparatus of claim 3, wherein the first angle is identical to the third angle.

5. The mobile X-ray imaging apparatus of claim 2, wherein the first and second sensors are light detection sensors.

6. The mobile X-ray imaging apparatus of claim 2, wherein the controller is further configured to determine a rotation direction of the driving wheel based on a detection signal pattern detected by the first and second sensors.

7. The mobile X-ray imaging apparatus of claim 2, wherein the controller is further configured to determine a rotation speed of the driving wheel based on cycles of detection signals detected by the first and second sensors.

8. The mobile X-ray imaging apparatus of claim 1, further comprising a control panel having a display configured to display an operating state of the mobile X-ray imaging apparatus,
  wherein the controller is further configured to determine a quasi-abnormal state of movement of the mobile X-ray imaging apparatus based on information detected by the motor encoder and the driving wheel rotation state detector, and control the display to display an attention mark when the quasi-abnormal state is detected.

9. The mobile X-ray imaging apparatus of claim 1, further comprising a warning lamp or a warning sound generator,
  wherein the controller is further configured to determine a quasi-abnormal state of movement of the mobile X-ray imaging apparatus based on information detected by the motor encoder and the driving wheel rotation state detector, and drive the warning lamp or the warning sound generator when the quasi-abnormal state is detected.

10. A method of operating a mobile X-ray imaging apparatus, the mobile X-ray imaging apparatus comprising a driving wheel capable of moving a main body and a driving wheel rotation state detector detecting a rotation state of the driving wheel, the method comprising:
  measuring a rotation speed of a drive motor by using a motor encoder; and
  detecting, by the driving wheel rotation state detector, a rotation state of the driving wheel driven by the drive motor,
  wherein the driving wheel rotation state detector comprises:
    a rotation state detection sensor located at the main body, and
    a bracket coaxially connected to the driving wheel and allowing the rotation state detection sensor to detect an ON/OFF state according to the rotation state of the driving wheel;
  wherein the drive motor is controlled based on information detected by the motor encoder and the driving wheel rotation state detector; and
  wherein an abnormal state of movement of the mobile X-ray imaging apparatus is determined based on information detected by the motor encoder and the driving wheel rotation state detector, and when an abnormal state is detected, driving of the drive motor is stopped.

11. The method of claim 10, wherein the bracket comprises a sensor bracket formed along a circumference of the bracket and a plurality of holes formed in the sensor bracket, and the rotation state detection sensor comprises first and second sensors arranged adjacent to the sensor bracket.

12. The method of claim 11, wherein the first and second sensors are arranged to satisfy three or more of:
  a first arrangement state in which the first and second sensors respectively face first and second holes of the plurality of holes at a first position of the bracket;
  a second arrangement state in which the bracket is rotated by a first angle from the first position to a second position at which the first sensor faces the first hole and the second sensor does not face the second hole;
  a third arrangement state in which the bracket is rotated by a second angle from the second position to a third position at which the first sensor and the second sensor do not face the first hole and the second hole, respectively; or
  a fourth arrangement state in which the bracket is rotated by a third angle from the third position to a fourth position at which the first sensor does not face the first hole and the second sensor faces a fourth hole that neighbors the second hole.

13. The method of claim 11, wherein a rotation direction of the driving wheel is determined based on a detection signal pattern detected by the first and second sensors.

14. The method of claim 11, wherein a rotation speed of the driving wheel is determined based on cycles of detection signals detected by the first and second sensors.

15. The method of claim 10, wherein the abnormal state is a state in which a rotation state of the drive motor exceeds a motor reference value or a rotation state of the driving wheel exceeds a wheel reference value.

16. The method of claim 10, wherein a quasi-abnormal state of movement of the mobile X-ray imaging apparatus is determined based on information detected by the motor encoder and the driving wheel rotation state detector, and when the quasi-abnormal state is detected, an attention mark is displayed on a display or a warning lamp or a warning sound generator is driven.

17. The method of claim 16, wherein the quasi-abnormal state is a state in which a rotation speed of the drive motor exceeds a first motor reference value, does not exceed a second motor reference value, or a state in which a rotation speed of the driving wheel exceeds a first wheel reference value, and does not exceed a second wheel reference value,
  wherein the second motor reference value is greater than the first motor reference value, and
  wherein the second wheel reference value is greater than the first wheel reference value.

18. The method of claim 17, wherein, when the rotation speed of the drive motor exceeds the second motor reference value or the rotation speed of the driving wheel exceeds the second wheel reference value, driving of the drive motor is stopped.

\* \* \* \* \*